(12) United States Patent
Howie et al.

(10) Patent No.: US 6,995,232 B2
(45) Date of Patent: Feb. 7, 2006

(54) SYNTHESIS OF POLYOL MEDIUM FATTY ACID POLYESTERS

(75) Inventors: John Keeney Howie, Oregonia, OH (US); Jared John Schaefer, Wyoming, OH (US); James Earl Trout, West Chester, OH (US)

(73) Assignee: Procter & Gamble, Cincinnati, OH (US)

( * ) Notice: Subject to any disclaimer, the term of this patent is extended or adjusted under 35 U.S.C. 154(b) by 537 days.

(21) Appl. No.: 10/058,520

(22) Filed: Jan. 28, 2002

(65) Prior Publication Data

US 2002/0143137 A1    Oct. 3, 2002

Related U.S. Application Data

(60) Provisional application No. 60/265,368, filed on Jan. 31, 2001.

(51) Int. Cl.
  *C08G 63/48* (2006.01)
(52) U.S. Cl. .................. 528/295.5; 528/274; 528/275; 526/66; 524/760; 524/764; 524/773; 524/777
(58) Field of Classification Search ............... 528/274, 528/275, 295.5; 526/66; 524/760, 764, 524/773, 777
See application file for complete search history.

(56) References Cited

U.S. PATENT DOCUMENTS

| 2,999,858 A | 9/1961 | Curtis |
| 3,600,186 A | 8/1971 | Mattson et al. |
| 3,957,855 A | 5/1976 | Miller |
| 3,963,699 A | 6/1976 | Rizzi et al. |
| 3,969,233 A | 7/1976 | Lucas |
| 4,334,061 A | 6/1982 | Bossier |
| 4,517,360 A | 5/1985 | Volpenhein |
| 4,518,772 A | 5/1985 | Volpenhein |
| 4,806,632 A | 2/1989 | McCoy et al. |
| 4,931,552 A | 6/1990 | Gibson et al. |
| 4,983,731 A | 1/1991 | Wagner et al. |
| 5,318,790 A | 6/1994 | Houston et al. |
| 5,348,676 A | 9/1994 | Takashima et al. |
| 5,422,022 A | 6/1995 | Chamberlin |
| 5,460,737 A | 10/1995 | Sakai et al. |
| 5,491,226 A | 2/1996 | Kenneally |
| 5,559,266 A | 9/1996 | Klaveness et al. |

FOREIGN PATENT DOCUMENTS

| EP | 0 550 526 B1 | 12/1996 |
| WO | WO 91/10368 A1 | 7/1991 |
| WO | WO 92/04360 A1 | 3/1992 |

OTHER PUBLICATIONS

Colbert, J.C.; "Sugar Esters Preparation and Applications", Noyes Data Corporation, London England, 1974; pp. 103-114.

*Primary Examiner*—Samuel A. Acquah
(74) *Attorney, Agent, or Firm*—Bryn R. Lorentz; Carl J. Roof

(57) ABSTRACT

Processes for the preparation of polyol fatty acid polyesters comprise heating a mixture of polyol, fatty acid ester, emulsifying agent and catalyst. In one embodiment, the fatty acid chains of the fatty acid ester have from about 6 to about 14 total carbon atoms and the emulsifying agent comprises a fatty acid soap having fatty acid chains of from about 16 to about 22 total carbon atoms.

28 Claims, No Drawings

SYNTHESIS OF POLYOL MEDIUM FATTY ACID POLYESTERS

CROSS REFERENCE TO RELATED APPLICATIONS

This application claims priority to U.S. Provisional Application No. 60/265,368, filed Jan. 31, 2001.

TECHNICAL FIELD

This invention relates to processes for the production of polyol fatty acid polyesters. More particularly, this invention relates to processes for preparing polyol fatty acid polyesters that include heating a mixture of polyol, fatty acid ester and catalyst. In one embodiment, the fatty acid chains of the fatty acid ester have from about 6 to about 14 total carbon atoms.

BACKGROUND OF THE INVENTION

Rizzi and Taylor, U.S. Pat. No. 3,963,699, describe a solvent-free transesterification process in which a mixture of a polyol (such as sucrose), a fatty acid lower alkyl ester (such as a fatty acid methyl ester), an alkali metal fatty acid soap, and a basic catalyst is heated to form a homogenous melt, to which is added excess fatty acid lower alkyl ester to form the higher polyol fatty acid polyesters.

Feuge et al., U.S. Pat. No. 3,714,144, and Feuge et al., *J. Amer. Oil Chem. Soc.*, 1970, 47(2), 56–60, disclose a solvent-free transesterification process that comprises mixing molten sucrose with esters of fatty acids and alkali-free sodium or potassium soaps under a partial vacuum. The teachings of Feuge et al. are primarily directed to the formation of lower esters; the only specific teaching by Feuge et al. of a method in which the percentage of sucrose esters having three or more fatty acid chains is greater than 35% of the total sucrose esters formed uses methyl carbitol palmitate as a fatty acid source.

Osipow et al., U.S. Pat. No. 4,380,616, disclose the preparation of sucrose mono- and di-esters by forming a transparent emulsion containing immiscible reactants and maintaining the transparent emulsions under appropriate conditions to permit reaction. Sucrose mono- and di-esters are formed using emulsions containing methyl fatty acid ester and sucrose. Osipow et al. also disclose the formation of mono- and di-glycerides using emulsions containing glycerine and methyl fatty acid esters or glycerol tri-esters.

Polyol fatty acid polyesters have been employed as food ingredients and in various industrial applications. Accordingly, there is a continuing need for new methods of preparing polyol fatty acid polyesters having various defined properties.

SUMMARY OF INVENTION

Accordingly, it is an object of this invention to provide processes for preparing polyol fatty acid polyesters, particularly of medium fatty acid chain length. It is an additional object of this invention to provide novel processes for the production of polyol fatty acid polyesters using fatty acid esters having fatty acid chains of from about 6 to about 14 total carbon atoms. It is another object of this invention to provide batch and continuous processes for the production of polyol fatty acid polyesters, in particular polyol polyesters wherein at least 50% of the polyol's hydroxyls are esterified.

In accordance with one aspect of the invention, processes for the preparation of polyol fatty acid polyesters comprise the step of heating a mixture of polyol, fatty acid ester, emulsifying agent and catalyst under conditions sufficient to cause reaction of the polyol and the fatty acid ester. The fatty acid chains of the fatty acid ester have from about 6 to about 14 total carbon atoms and the emulsifying agent comprises a fatty acid soap having fatty acid chains of from about 16 to about 22 total carbon atoms.

In accordance with a further aspect of the invention, processes for the preparation of higher polyol fatty acid polyesters comprise heating a mixture of polyol, fatty acid ester and catalyst. The fatty acid chain of the fatty acid ester has from about 6 to about 14 total carbon atoms and at least 50% the polyol's hydroxyl groups are esterified.

In accordance with yet another aspect of the invention, processes for the preparation of higher polyol fatty acid polyesters comprise heating a mixture of polyol, fatty acid ester and catalyst to form a polyol fatty acid polyester. The polyol fatty acid polyester has a pour point of not greater than about −15° C.

The processes of the invention provide polyol fatty acid polyesters of medium fatty acid chain length having desirable properties. In one embodiment, the resulting polyol fatty acid polyesters have a pour point of not greater than −15° C., which makes the polyesters suitable for use in low temperature applications.

These and additional objects and advantages will be more fully apparent in view of the following detailed description.

DETAILED DESCRIPTION

The present invention encompasses continuous and batch transesterification processes for synthesizing polyol fatty acid polyesters, in particular highly esterified polyol fatty acid polyesters.

As used herein, the term "polyol" is intended to include any aliphatic or aromatic compound containing at least two free hydroxyl groups. In practicing the processes disclosed herein, the selection of a suitable polyol is simply a matter of choice. For example, suitable polyols may be selected from the following classes: saturated and unsaturated straight and branched chain linear aliphatic; saturated and unsaturated cyclic aliphatic, including heterocyclic aliphatic; or mononuclear or polynuclear aromatics, including heterocyclic aromatics. Carbohydrates and glycols are exemplary polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particular classes of materials suitable for use herein include monosaccharides, disaccharides and sugar alcohols. Other classes of materials include sugar ethers and alkoxylated polyols, such as polyethoxy glycerol.

Polyol fatty acid polyester products include sucrose polyesters having on average at least four, preferably at least about five, ester linkages per sucrose molecule. In one embodiment, fatty acid chains of the polyol fatty acid polyester may be branched or linear, and saturated or unsaturated. The fatty acid chains of the fatty acid esters have from about 6 to about 14 total carbon atoms. In one embodiment, the fatty acid chains of the polyester may be branched or linear and may be formed from fatty acid esters having fatty acid chains of from about 8 to about 12 total carbon atoms. In yet another embodiment, the fatty acid chains of the fatty acid ester have from about 8 to about 10 total carbon atoms.

Other suitable polyol fatty acid polyesters are esterified linked alkoxylated glycerins, including those comprising polyether glycol linking segments, as described in U.S. Pat. No. 5,374,446 and those comprising polycarboxylate linking segments, as described in U.S. Pat. Nos. 5,427,815 and 5,516,544, Additional suitable polyol fatty acid polyesters are esterified epoxide-extended polyols of the general formula $P(OH)_{A+C} (EPO)_N (FE)_B$ wherein $P(OH)$ is a polyol, A is from 2 to about 8 primary hydroxyls, C is from about 0 to about 8 total secondary and tertiary hydroxyls, A+C is from about 3 to about 8, EPO is a $C_3$–$C_6$ epoxide, N is a minimum epoxylation index average number, FE is a fatty acid acyl moiety and B is an average number in the range of greater than 2 and no greater than A+C, as described in U.S. Pat. No. 4,861,613. The minimum epoxylation index average number has a value generally equal to or greater than A and is a number sufficient so that greater than 95% of the primary hydroxyls of the polyol are converted to secondary or tertiary hydroxyls. Preferably the fatty acid acyl moiety has a $C_7$–$C_{23}$ alkyl chain.

Suitable esterified epoxide-extended polyols include esterified propoxylated glycerols prepared by reacting a propoxylated glycerol having from 2 to 100 oxypropylene units per glycerol with $C_{10}$–$C_{24}$ fatty acids or with $C_{10}$–$C_{24}$ fatty acid esters, as described in U.S. Pat. Nos. 4,983,329 and 5,175,323, respectively, and esterified propoxylated glycerols prepared by reacting an epoxide and a triglyceride with an aliphatic polyalcohol, as described in U.S. Pat. No. 5,304,665 or with an alkali metal or alkaline earth salt of an aliphatic alcohol, as described in U.S. Pat. No. 5,399,728. Other polyols include acylated propylene oxide-extended glycerols having a propoxylation index of above about 2, preferably in the range of from about 2 to about 8, more preferably about 5 or above, wherein the acyl groups are $C_8$–$C_{24}$, preferably $C_{14}$–$C_{18}$, compounds, as described in U.S. Pat. Nos. 5,603,978 and 5,641,534 and fatty acid-esterified propoxylated glycerols, as described in U.S. Pat. Nos. 5,589,217 and 5,597,605.

Other suitable esterified epoxide-extended polyols include esterified alkoxylated polysaccharides. Preferred esterified alkoxylated polysaccharides are esterified alkoxylated polysaccharides containing anhydromonosaccharide units, more preferred are esterified propoxylated polysaccharides containing anhydromonosaccharide units, as described in U.S. Pat. No. 5,273,772.

As used herein, the term "partially esterified polyol" is intended to include those esters of the polyol wherein less than about 50% of the hydroxyl groups of polyol have been esterified. As used herein, the term "degree of esterification" refers to the percentage of hydroxyl groups of a polyol that have been esterified.

As used herein, the term "highly esterified polyol fatty acid polyesters" is intended to include those esters of the polyol wherein at least 50%, of the hydroxyl groups are esterified. In one embodiment of the invention at least about 70%, preferably at least about 75%, of the hydroxyl groups of the polyol are esterified, while in another embodiment of the invention at least about 90%, preferably at least about 95%, of the hydroxyl groups of the polyol are esterified.

In one embodiment, the polyol fatty acid polyesters, particularly sucrose fatty acid polyesters, have an average of at least 4 fatty acid groups per molecule. In another embodiment of the invention, the polyol fatty acid polyester is a sucrose fatty acid polyester having an average of at least 5 fatty acid groups per molecule, while in another embodiment the sucrose fatty acid polyesters have an average of from about 5 to about 8 fatty acid groups per molecule. In yet another embodiment, the polyol polyester is a sucrose polyester wherein at least about 75% of the sucrose polyester comprises octaester.

A process for the preparation of higher polyol fatty acid polyesters comprises the step of forming a reaction mixture comprising polyol, medium chain fatty acid ester, catalyst and, optionally, an emulsifying agent, and heating the reaction mixture. The process may be conducted in one step, wherein the original reaction mixture contains a stoichiometric excess of fatty acid ester. Alternatively, the process may be conducted in two or more steps wherein, after the initial heating, the process further comprises the step of subsequently adding fatty acid ester in addition to that originally employed. In one embodiment, the reaction mixture is stirred, and may be stirred vigorously.

As used herein, reference to a fatty acid compound having fatty acid chains of a particular length is intended to mean that a majority of the fatty acid chains, i.e., greater than 50 mol % of the fatty acid chains, have the stated length. In a more specific embodiment, the fatty acid compounds have greater than about 60 mol %, and more specifically greater than about 75 mol %, of fatty acid chains of the stated length. As used herein "medium chain fatty acid ester" is intended to include fatty acid esters in which the fatty acid chains have a total of from about 6 to about 14, typically from about 8 to about 12, carbon atoms. The medium chain fatty acid esters may be branched or unbranched, saturated or unsaturated, and hydrogenated or unhydrogenated.

In one embodiment of the invention, the medium chain fatty acid ester is selected from the group consisting of esters having a total of 8, 10, 12 and 14 carbon atoms, and mixtures thereof. Medium chain fatty acid esters obtained from coconut oil, either nonfractionated, whole cut coconut oil or fractionated coconut oil, and mixtures thereof may be used. Tropical oils, including palm and palm kernel oil, in fractionated or nonfractionated form may also be employed. In one embodiment, the fatty acid ester is a methyl fatty acid ester. Exemplary esters include $C_8$ methyl ester, $C_{10}$ methyl ester, $C_{12}$ methyl ester, $C_{14}$ methyl ester and mixtures thereof. One skilled in the art will of course appreciate that the nonfractional whole cut coconut oil will contain a majority of $C_{12}$ and $C_{14}$ fatty acid chain lengths and a minority of $C_{16}$ and $C_{18}$ fatty acid chain lengths.

In one embodiment, the medium chain fatty acid ester is prepared from an acid selected from the group of acids having the structure:

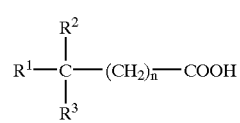

wherein $R^1$ is a hydrocarbon, $R^2$ and $R^3$ are independently selected from hydrogen and a hydrocarbon and n is from 0 to about 11. In one embodiment, $R^2$ and $R^3$ each is hydrogen. In another embodiment, $R^2$ is hydrogen and $R^3$ is a hydrocarbon other than methyl. $R^1$ (and $R^2$ and $R^3$ when relevant) hydrocarbons may be branched or unbranched and saturated or unsaturated. In one embodiment, the medium chain fatty acid ester is prepared from an acid having the structure:

$$R^1R^2CH\text{—}COOH$$

wherein $R^1$ is a $C_{1-4}$ hydrocarbon and $R^2$ is $C_{1-4}$ hydrocarbon, wherein the total number of carbon atoms in the acid is from 6 to 14. In another embodiment the medium chain fatty acid ester is prepared from an acid having the structure:

$$R^1R^2CH\text{—}(CH_2)_n\text{—}COOH$$

wherein $R^1$ is methyl, $R^2$ is $C_{1-2}$ hydrocarbon, and n is at least 1, wherein the total number of carbon atoms in the acid is from 6 to 14.

While not intending to be bound by theory, the fatty acid ester that is employed in the process of the invention contributes to forming a polyol polyester product having an advantageously low pour point. Within the scope of the present specification, pour point is measured according to ASTM D 97-96A. In one embodiment, the polyol fatty acid polyester has a pour point of not greater than about $-5°$ C., more preferably not greater than about $-15°$ C. In another embodiment, the polyol fatty acid polyester has a pour point not greater than about $-25°$ C. In a further embodiment, the polyol fatty acid polyester has a pour point not greater than about $-30°$ C. While not being bound by theory, it is believed that the degree of branching of the medium chain fatty acid ester affects the pour point of the polyol polyester formed with the fatty acid ester.

Suitable basic compounds to be used as a basic reaction catalyst in the processes of the invention include alkali metals such as sodium, lithium and potassium; alloys of two or more alkali metals such as sodium-lithium and sodium-potassium alloys; alkali metal hydrides, such as sodium, lithium and potassium hydride; alkali metal lower ($C_1$–$C_4$) alkyls such as butyl-lithium; and alkali metal alkoxides of lower ($C_1$–$C_4$) alcohols, such as lithium methoxide, potassium t-butoxide, potassium methoxide, and/or sodium methoxide. Other suitable basic compounds include carbonates and bicarbonates of alkali metals or alkaline earth metals.

In one embodiment of the invention, basic catalysts include potassium carbonate, sodium carbonate, barium carbonate, or mixtures of these compounds having particle sizes that are less than about 100 microns, preferably less than about 50 microns. It has been found that when these catalysts are used, increased yields of light-colored higher polyol polyesters are obtained as compared to essentially identical reactions carried out using more conventional catalysts, such as sodium hydride, potassium hydride, soap, or sodium methoxide. These catalysts can be used in admixture with the more conventional basic catalysts, described above. Potassium carbonate and/or potassium methoxide are also suitable catalysts. The use of these catalysts is further disclosed in U.S. Pat. No. 4,517,360 to Volpenhein. For the transesterification reaction, the level of basic catalyst is typically from about 0.01 to about 0.5 moles of catalyst per mole polyol. In one embodiment, the molar ratio of catalyst to polyol is from about 0.01:1 to about 0.1:1, preferably from about 0.02:1 to about 0.05:1, while in another embodiment, the molar ratio of catalyst to polyol ranges from about 0.1:1 to about 0.3:1.

In one embodiment, the reaction mixture comprises emulsifying agent. As used herein, the term "emulsifying agent" is intended to include substances capable of emulsifying the mixture of unesterified polyol and fatty acid ester, such as soaps, partially esterified polyols, bile salts and solvents. The presence of an emulsifying agent, such as soap, may be desirable in the initiation of the reaction, but may not be desired after the polyol has been partially esterified and there is sufficient partially-esterified polyol to maintain the homogeneity of the reaction mixture in the absence of emulsifying agent. At this stage, the emulsifying agent may be removed by any suitable means.

When soap is included in the reaction mixture, the absolute level of soap may be kept low but should be at least enough to dissolve the polyol at an acceptable rate. Therefore, the level of soap can be reduced as a result of using smaller particle polyol and/or reaction conditions that favor the solubilizing of the polyol. The level of soap is typically from about 0.001 to about 0.75, preferably from about 0.01 to about 0.5, moles of soap per mole of polyol. In a further embodiment, the level of soap is about 0.05 to about 0.10 moles per mole of polyol. The soap may be used in combination with another emulsifier, preferably with the lower esters of the polyol and the fatty acid that are present either by addition as part of the initial reaction mixture, or by back-mixing. Suitable lower polyol polyesters are sucrose lower polyesters having no more than about 4 esters per molecule sucrose.

Suitable soaps include alkali metal fatty acids soaps. As used herein, the term "alkali metal fatty acid soaps" is intended to include the alkali metal salts of saturated or unsaturated fatty acids having from about 8 to about 24 total carbon atoms. In various embodiments, the soap has from about 8 to about 22, from about 8 to about 18, from about 16 to about 22, or from about 16 to about 18, total carbon atoms. Suitable alkali metal fatty acid soaps include, for example, lithium, sodium, potassium, rubidium, and cesium salts of the fatty acids described herein. Mixtures of fatty acids derived from soybean oil, sunflower oil, safflower oil, cottonseed oil and corn oil may be used to form soaps. Accordingly, alkali metal fatty acid soaps include, for example, the potassium soap made from soybean oil fatty acids. In one embodiment the soap is a potassium soap of hydrogenated fatty acids containing from about 8 to about 24, more preferably from about 16 to about 22, carbon atoms in the fatty acid chains. The use of such soaps is further disclosed in U.S. Pat. No. 5,491,226 (Kenneally).

In one embodiment, the soap is a behenate salt, for example potassium behenate. In another embodiment, the emulsifying agent is a fatty acid soap having a greater number of total carbon atoms than the total number of carbon atoms in the fatty acid chain of the fatty acid ester used to form the polyol polyester.

The reaction mixture may be substantially free of added solvent, or may be free of added solvent. As used herein "added solvent" refers to solvent added to the reaction mixture, and is not intended to include any alcohol formed during the reaction, while "substantially free of added solvent" is intended to refer to reaction mixtures having no more than 10% by weight of the mixture, added solvent. Alternatively, the reaction mixture may comprise added solvent. Suitable solvents include dimethylformamide (DMF), formamide, dimethyl sulfoxide or pyridine.

As the transesterification reaction proceeds, a lower alcohol is formed as a by-product. In order to promote the reaction, the alcohol by-product is preferably removed from the reaction mixture. Without being limited by theory, it is believed that reducing the partial pressure of lower alcohol in the headspace below that which is in equilibrium with the liquid phase results in alcohol removal from the liquid phase reaction mixture. Many techniques known in the art can be used effectively and efficiently to reduce the partial pressure of the lower alcohol. Vacuum, with or without inert gas sparging into the vapor or liquid phases, can be used to remove the alcohol and promote the reaction. Alternatively, inert gas sparging can be used at atmospheric or greater pressures to promote alcohol removal. Sparging inert gas into the liquid has the added benefit of increasing surface area available for mass transfer of lower alcohol into the gas phase. As inert gas sparging is increased, the vacuum level may be decreased in order to achieve a desired lower alcohol partial pressure.

Many techniques used to reduce the partial pressure of lower alcohol also reduce the partial pressure of lower alkyl ester, ultimately resulting in transfer of lower alkyl ester from the liquid phase into the vapor phase. Since the lower alkyl esters are needed for esterification onto the polyol, it is generally advantageous to reflux them (i.e., separate them from the vapor phase leaving the reaction and return them to the reaction mixture). Refluxing may be performed using a mechanical refluxing system such as, for example, a reflux column, or by distilling and condensing the fatty acid esters and returning the condensed esters to the reaction mixture. Alternatively, a larger excess of lower alkyl esters can be added to the reaction mixture such that lower alkyl esters lost during lower alcohol removal do not affect the rate or extent of polyol esterification.

In one embodiment the transesterification reaction occurs in one step. The entire desired amount of fatty acid ester to be reacted with the polyol is mixed with polyol, catalyst and any emulsifying agent to form a reaction mixture and the reaction mixture is then heated; there is no additional fatty acid ester added at a later reaction point. The reaction mixture is preferably heated to a temperature of from about 120° C. to about 160° C., preferably at about 135° C., the reaction may be conducted at any suitable pressure, below, at or above atmospheric pressure. In one embodiment, the one step reaction is conducted at a pressure of from about 5 to about 300 mm Hg without inert gas sparge, preferably from about 60 to about 190 mm Hg. In another embodiment, the one step reaction is conducted at a pressure of from about 5 to about 1000 mm Hg utilizing a nitrogen sparge to keep the combined partial pressures of lower alkyl ester and lower alcohol in a range of from about 5 to about 300 mm Hg. In a further embodiment, the one step reaction is conducted at a pressure of from about 60 to about 800 mm Hg utilizing a nitrogen sparge to keep the combined partial pressures of lower alkyl ester and lower alcohol in a range of from about 60 to about 190 mm Hg. In the one step reaction, the molar ratio of the fatty acid chains of the lower alkyl ester to the hydroxyl groups of the polyol is preferably in a stoichiometric excess, i.e., greater than 1:1. In one embodiment, the polyol is sucrose, and the mole ratio of fatty acid ester/sucrose is at least about 8:1, more preferably 11:1, while in another embodiment the mole ratio of fatty acid ester/sucrose is at least about 12:1. In yet a further embodiment the mole ratio of fatty acid ester/sucrose is from about 8:1 to about 14:1. In one embodiment, the mole ratio of fatty acid ester/sucrose/emulsifying agent is from about 8:1:0.75 to about 12:1:0.05, while in yet another embodiment the mole ratio is from about 11:1:0.75 to about 12:1:0.01. In a further embodiment of the single step reaction and the mole ratio of fatty acid ester/polyol/emulsifying agent is about 12:1:0.06.

In one embodiment of the single step process, a mixture of a polyol, alkali metal fatty acid soap, basic catalyst selected from potassium carbonate, sodium carbonate, barium carbonate and mixtures thereof and excess fatty acid lower alkyl ester is heated to form the polyol fatty acid polyester.

In another embodiment, the polyol-fatty acid ester reaction occurs in at least two steps. In the first step, the fatty acid ester and polyol are employed in amounts sufficient to provide a molar ratio of fatty acid chains to hydroxyl groups of the polyol which is less than or equal to the stoichiometric equivalent, i.e., not greater than about 1:1. In one embodiment, the polyol is sucrose and the molar ratio of fatty acid ester to sucrose is at least about 3:1, more preferably at least about 4:1, and in a further embodiment is from about 4:1 to about 8:1. In a further embodiment, the molar ratio is about 5:1. In a later step, after the original mixture is heated to cause reaction of the fatty acid ester and the polyol, additional fatty acid esters and, optionally, more reactive catalyst, are added. The fatty acid ester may be added to raise the overall ratio of fatty acid groups to the polyol above the theoretical, fully esterified level, e.g., by at least about 25%, or even by at least about 50%. The catalyst in any later step can be the same as or different from the catalyst in the initial step. In one embodiment, the catalyst in the initial step is potassium carbonate or alkali metal hydroxide at a low level and, in any later step, the catalyst is either the same as the initial catalyst or is potassium or sodium methoxide.

For example, an initial heterogeneous mixture of polyol, fatty acid ester, catalyst and, optionally, emulsifying agent, is heated, forming a homogeneous melt of partially esterified polyols (lower polyesters) and unreacted starting materials in from about one to about four hours. As used herein, the term "lower polyesters" refers to those esters of the polyol wherein up to about 50% of the hydroxy groups of polyol have been esterified. In the case of sucrose, the primary sucrose fatty acid lower esters are mono, di, and/or tri-esters.

In the second step of the transesterification process, excess fatty acid lower alkyl ester is added to the homogeneous melt formed in the first step. As used herein, the term "excess" is intended to be an amount beyond that required to form the theoretical, fully esterified polyol fatty acid polyesters. When fatty acid methyl esters are used, it is preferred that, after the excess esters are added to the reaction mixture, the mixture is heated to a temperature of from about 120° C. to about 160° C., preferably at about 135° C., at a pressure and with inert gas sparge sufficient to maintain the combined partial pressures of lower alkyl ester and lower alcohol in a range of from about 5 to about 300 mm Hg, preferably from about 60 to about 190 mm Hg. The reaction time for the second step is generally less than about 10 hours, and may be between about 2 to about 8 hours. During the second step, the partially esterified polyol is further esterified to provide highly esterified polyol fatty acid polyesters.

The transesterification reaction between the polyol and the fatty acid ester can be conducted in any reactor conventionally employed for polyol fatty acid polyester preparation, including, but not limited to batch, semi-batch and continuous reactors. Column reactors, packed or multistage, are suitable for use in the transesterification reaction. Plug flow column reactors are also suitable.

In either the one step or the two step process, the reaction mixture is heated to a temperature sufficient to facilitate reaction of the polyol and the fatty acid ester. In one embodiment, the reaction mixture is heated to a temperature of at least about 115° C. In another embodiment, the reaction mixture is heated to a temperature in the range from about 115° C. to about 150° C. In another embodiment, the reaction mixture is heated to a temperature in the range from about 120° C. to about 140° C., while in yet another embodiment the reaction mixture is heated to a temperature of about 135° C.

The reaction mixture is heated under a pressure sufficient to facilitate the reaction and, as noted above, may be below, at or above atmospheric pressure. In one embodiment, the pressure is sufficient to reflux excess fatty acid esters during the reaction as disclosed above. In one embodiment, the reaction mixture is heated under a pressure sufficient to maintain a substantially constant reflux rate of the fatty acid ester. As used herein, a "substantially constant reflux rate" is intended to mean the reflux rate does not vary by more than about 10%. The reaction mixture may be heated at a pressure and with inert gas sparge sufficient to maintain the combined partial pressures of lower alkyl ester and lower alcohol in a range of from about 5 mm to about 300 mm Hg, and preferably from about 60 mm to about 190 mm Hg. In one embodiment the pressure is decreased between the start of heating and the end of the heating in order to maintain a substantially constant reflux rate of the fatty acid ester. For example, the pressure may be decreased from a pressure of about 250 mm Hg without inert gas sparging at the start of heating to a pressure of about 65 mm Hg without inert gas sparging at the end of the heating. In another embodiment, the pressure is held constant while the inert gas sparge is increased between the start and end of heating. In yet another embodiment, the pressure is decreased while the inert gas sparge is increased between the start and end of heating.

If soap is used as an emulsifier, after the average degree of esterification reaches about 60%, the soap emulsifier is generally no longer needed to facilitate the reaction and, therefore, can be removed. Removal of soap can be accomplished by known techniques, e.g., by filtration, centrifugation, etc., since the soap is relatively insoluble in the reaction mixture at high degrees of esterification. The filtered reaction mixture typically has a soap level of less than about 0.5 moles of soap per mole polyol, preferably less than about 0.05 moles of soap per mole polyol. On a weight basis, about 0.5 moles of soap per mole polyol is generally from about 4% to about 10% soap, by weight of the mixture, and about 0.05 moles of soap per mole polyol is generally from about 0.4 to about 1% soap, by weight of the mixture; one of ordinary skill will appreciate that the weight percent value is dependent on the length of the fatty chain on the soap, the length of the fatty chain esterified to the polyol, and the molecular weight of the polyol in the mixture.

Separation of any remaining fatty acid ester from the polyol fatty acid polyester product can be effected with many different equipment designs, including but not limited to batch, continuous, and semi-continuous. For example, fatty acid methyl esters can be distilled by batch (single stage or multi stage) distillation or by continuous distillation. Additionally, the use of wiped film evaporators is advantageous.

The resulting polyol fatty acid polyester product can be centrifuged, water-washed, and bleached, for example, with bleaching clays or silica gel, for refinement. Centrifugation can be performed, for example, with a disc stack centrifuge. Water-washing can be done, for example, in a stirred tank. In one embodiment, water washing in a stirred tank employs a water level of from about 5% to about 18% by weight of unrefined polyester, and a mixing time of from about 10 to about 30 minutes. The water phase can be separated by gravity settling. Either co-current or counter-current columns may be employed.

The polyol polyester product may be further purified as desired. In one embodiment, processing in accordance with the method of Houston et al., U.S. Pat. No. 5,318,790, may be employed. For example, a process for removing undesirable reaction products from higher polyol fatty acid polyesters and for preventing or inhibiting oxidation, hydrolysis and the formation of dimer methyl esters during synthesis of the polyol fatty acid polyester may comprise treating the crude polyesters with a silica gel. In one embodiment the polyol polyester product is treated during or following the refining steps with a silica gel, and, optionally, is heat-treated and/or treated to remove volatiles. The polyol polyester may be heat treated to reduce the content of peroxide groups and to remove undesirable volatile materials by, for example, steam stripping, preferably at a temperature below about 230° C. The removal of undesirable volatile materials may also be accomplished by any other suitable method, such as solvent extraction; straight distillation under reduced pressure; extraction with other gases to reduce partial vapor pressure; absorption on the materials selected from the group consisting of gels, alumina, charcoal, molecular sieves, and porous polymers; steam deodorization; or combinations thereof.

In one embodiment the peroxide value of the polyol fatty acid polyester 120 minutes after treatment with the silica gel is less than about 400 ppm. The polyol fatty acid polyester contains less than about 100 ppm of free fatty acids after treatment with the silica gel. In one embodiment, the color of the finished product should be less than about 6.0, preferably less than about 4.0, more preferably less than about 3.0, Lovibond Red.

Suitable mixing vessels for water-washing include multistage columns with agitation. Multistage columns suitable for use with the present invention include, but are not limited to, rotary disc contractors, Oldshue-Rushton extractors, Scheibel extraction towers, Kuhni towers, and the like. These columns are discussed by Perry, et al. *Chemical Engineers Handbook,* 6th Edition, 1984, pages 21–77 to 21–79. The columns in Perry et al. are schematically shown with counter-current flow. A heavy liquid is fed from the top of a vertical column and removed from the bottom with a light liquid fed near the bottom and extracted near the top. The two streams of the present invention can be fed counter-current, i.e., the streams flow through the column in opposite directions, or co-current, i.e., both streams flow through the column in the same direction. When the two streams are fed at or near the same end of the column, they are normally removed at or near the opposite end of the column.

Baffles can be provided between stages within the column wherein the size and shape of the opening in the baffle is designed to provide the desired residence time within each stage and other process conditions. Likewise, within each stage, an impeller can be provided, and typically the impellers are connected to a single shaft that runs through the column. Thus, one shaft can drive all of the impellers, maintaining the agitation speed relatively constant within different stages. However, as can be appreciated, impellers with independent drive motors and/or gears can be provided at individual stages or between stages so that the respective impeller speeds vary from one stage to the next. Agitation speed within the column and within individual stages, the size and shape of the baffle openings separating stages and the number of stages are all design criteria which can be varied to achieve a desired purification.

Multistage columns can be provided with "calming" zones at one or both ends of the column. If a calming zone is provided, two phases can be separated through the use of two extraction ports, i.e., a first port for extracting the first phase and a second port for extracting the second phase.

The polyol polyester can then be dried to a moisture content of less than about 0.1%, for example by use of a vacuum dryer. Silica gel bleaching can be conducted, for example, by contacting dry silica with the polyol polyester in a stirred tank for about 30 minutes; the silica level is preferably from about 0.5% to about 1% by weight of the crude reaction mixture. The silica gel can be separated from the polyol polyester with a filter press.

In one embodiment, the processes of the invention for preparing the polyol polyesters comprise one or more of the following characteristics: low levels of soap emulsifying agent, catalyst and/or excess fatty acid ester; reduced size polyol particles; removal of extraneous particulate material during the reaction; low temperature and/or high pressure, particularly with increased mass transfer area; backmixing in the initial stages and plug-flow conditions in the final stages. Mixtures of these characteristics in accordance with the method of Appleby et al., WO92/04360 are also suitable.

More particularly the process of preparing the polyol polyesters may comprise one or more of the following steps:

(1) reducing the particle size of a polyol which is a particulate solid by mechanical size reduction to a particle size of less than about 100 microns;

(2) removing the soap from the reaction mixture by filtration or centrifugation in a continuous process once the degree of esterification is greater than about 60% and the soap is insoluble in the reaction mixture;

(3) removing unreacted polyol having particle sizes above about one micron before any soap that is present becomes insoluble, in a continuous process;

(4) assisting the removal of volatile alcohol by increasing the mass transfer area of the reaction mixture when the pressure above the reaction mixture in the final stages of the esterifying reaction is maintained at from about 15 to about 300 mm Hg;

(5) carrying out the initial stage of the esterifying reaction in a continuous manner under conditions of backmixing suitable for maintaining within the reaction mixture a level of lower partial fatty acid esters sufficient to emulsify the reaction mixture; and (6) carrying out at least a final stage of the esterifying reaction in a continuous manner under conditions approaching plug-flow conditions after the degree of esterification of said polyol has reached at least about 50%.

In one embodiment, the initial reaction stage is carried out in a continuous reaction vessel having stirring means, such as a continuous stirred tank reactor. There may be one in-going reactant stream in the initial stage. In a further embodiment, the partial vapor pressure of the volatile alcohol in the initial reaction stage is less than about 25 mm Hg. The partial vapor pressure of the volatile alcohol may be maintained by sparging with an inert gas. In another embodiment, one or more subsequent reaction zones are provided in a tray reactor.

In another embodiment of the invention, methyl esters having a level of monoglycerides below about 500 ppm, an undetectable level of di- and triglyceride and a glycerine level of less than about 200 ppm are prepared and then used in a two-stage, solvent-free transesterification reaction to prepare the polyol polyesters, in accordance with the method of Kenneally, U.S. Pat. No. 5,491,226. The resulting polyol polyesters have levels of triglyceride below about 0.5%, by weight.

In one particular embodiment, the fatty acid monohydric lower alkyl esters having a level of monoglycerides below about 500 ppm, a non-detectable level of di- and triglyceride and a glycerine level below about 200 ppm are prepared by reacting a fatty acid glycerol ester with a monohydric lower alkyl alcohol in the presence of a suitable catalyst to produce a mixture of fatty acid monohydric lower alkyl esters, fatty acid glycerol esters and glycerol; and separating the mixture into a glycerine phase and a fatty acid monohydric lower alkyl ester-containing phase. The fatty acid monohydric lower alkyl ester-containing phase preferably has a level of residual mono-, di-, and triglycerides less than about 10%, by weight. More preferably, the level of glycerides is less than about 5%, even more preferably less than about 2%, by weight. The process then further comprises water washing the fatty acid monohydric lower alkyl ester-containing phase under conditions suitable to provide a fatty acid monohydric lower alkyl ester phase containing less than about 300 ppm glycerine, and distilling the fatty acid monohydric lower alkyl esters under conditions suitable to provide fatty acid monohydric lower alkyl esters having a level of monoglycerides below about 500 ppm, a non-detectable level of di- and triglyceride and a glycerine level below about 200 ppm. The fatty acid methyl ester-containing phase may be washed with from about 2% to about 50% by weight water in a stirred tank, a column or an in-line static mixer with a residence time of from about 0.5 to about 60 minutes at a temperature of from about 20° C. (68° F.) to about 95° C. (203° F.), preferably from about 21° C. (70° F.) to about 93° C. (200° F.), at about atmospheric pressure.

In one embodiment, the fatty acid methyl ester-containing phase is washed with from about 10% to about 25% water, more specifically from about 15% to about 20% water, for from about 5 to about 15 minutes at a temperature of from about 35° C. to about 80° C., preferably from about 50° C. to about 77° C. In one embodiment distillation may occur at a pressure of from about 0.5 to about 5 mm Hg and a temperature of from about 150° C. to about 260° C., preferably from about 170° C. to about 260° C. In another embodiment, distillation may occur at a pressure of from about 0.005 mm Hg to about 30 mm Hg and a temperature of from about 120° C. to about 305° C.

The fatty acid monohydric lower alkyl esters and polyol are transesterified to provide a polyol fatty acid polyester having a triglyceride level of less than 0.5%. In one embodiment, the transesterification process is a solvent-free two-stage process wherein the first stage comprises forming polyol fatty acid partial esters from a reaction mixture containing a polyol having more than 4 esterifiable hydroxy groups and at least a portion of the fatty acid esters of the easily removable alcohol in the presence of an effective amount of a basic catalyst and optionally an effective amount of soap emulsifier, and wherein the second stage comprises forming highly esterified polyol fatty acid polyesters from a reaction mixture containing the polyol fatty acid partial esters, the remaining portion of the fatty acid esters and an effective amount of a basic catalyst. The process may be performed in a continuous method or in a batch method.

The process for making the polyol polyester may include the steps of finishing the polyol fatty acid polyester by heating and isolating the polyol polyester in accordance with the method of Samara, U.S. Pat. No 5,559,226. In one embodiment the process for making the polyol polyesters comprises the steps of heating a mixture of a polyol, a fatty acid ester, an emulsifier and a catalyst to form a reaction mixture; adding more fatty acid ester to the reaction mixture to form an unrefined polyol polyester; adding an alkaline material to the unrefined polyol polyester in an amount such that the resulting mixture has a pH of from about 6.5 to about 8.5, preferably from about 6.5 to about 7.5, more preferably about 7; finishing the polyol fatty acid polyester by heating to a temperature ranging from about 190° C. (374° F.) to about 290° C. (554° F.), and isolating the polyol polyester. This embodiment may be useful where an unsaturated product is desired. The polyol fatty acid polyester may be finished by thermal evaporation or by high temperature steam distillation. Preferably the oxygen level during the finishing step is less than about 0.1%.

In one embodiment, after the addition of the alkaline material, the resulting mixture is maintained at a temperature from about 20° C. to about 60° C., preferably from about 32° C. to about 50° C., for from about 5 to about 30 minutes. The alkaline material may be in the form of a base solution comprising a base selected from the group consisting of alkali metal and alkaline earth metal hydroxides, carbonates, oxides, and mixtures thereof; and an organic solvent selected from the group consisting of alcohols, ethers, and mixtures thereof. Suitable alkali metals and alkaline earth metals may be selected from the group consisting of lithium, sodium, potassium, magnesium, calcium, barium, and mixtures thereof. Suitable solvents include alcohols selected from the group consisting of monohydric, polyhydric, and mixtures of mono- and polyhydric alcohols. In one embodiment, the alcohol is a $C_1$ to $C_{10}$ monohydric alcohol such as methyl, ethyl, propyl, isopropyl, butyl, isobutyl, sec butyl, pentyl, isopentyl, tert-pentyl, heptyl, octyl, benzyl, and/or phenylethyl alcohol. In other embodiments, the organic solvent is selected from the group consisting of ethylene glycol, propylene glycol, glycerol and mixtures thereof, or from the group consisting of ethyl ether, propyl ether, isopropyl ether, butyl ether, and mixtures thereof.

Polyol polyesters having at least one unsaturated fatty acid may be post-hydrogenated in accordance with the method of McCoy et al., U.S. Pat. No. 4,806,532. In one embodiment, the polyol polyesters having at least one unsaturated fatty acid are post-hydrogenated with hydrogen gas in the presence of a catalytically effective amount of hydrogenation catalyst, at a temperature of from about 120° C. to about 230° C., preferably from about 170° C. to about 210° C., more preferably from about 185° C. to about 210° C. In one embodiment, the hydrogen pressure is at least about 20 psig, preferably at least about 40 psig, more preferably at least about 45 psig.

Typically, hydrogen is first brought into contact with the polyesters, and the hydrogen-laden polyesters are then brought into contact with the catalyst by mechanical means. In the usual type of equipment, a suspension of catalyst and polyester is agitated in a closed vessel in an atmosphere of hydrogen. Agitation of the catalyst-polyester mixture promotes dissolution of hydrogen in the polyester and continuously renews the polyester at the catalyst surface. The time of hydrogenation is a function of the temperature, pressure, type of polyol polyester, and the type of catalyst. The polyol polyester may be hydrogenated to a particular Refractive Index endpoint (as an indicator of Iodine Value), depending on the kind of product desired.

The polyol polyesters resulting from the processes of the invention generally exhibit low pour point temperatures and therefore are advantageous for use in various applications where low pour point temperatures are desirable. For example, the polyol polyesters may be used in waxes, paints and other coating materials, for example, alkyd-based paints and varnishes, and lubricants. The polyol polyesters may be particularly suitable for use in lubricants for gas or diesel two-stroke engines, chain saws and the like. The polyol polyesters may also be suitable for use in industrial gear oils, metal working fluids, annealing fluids, mining fluids, drilling muds, and like applications to provide lubricating properties. The polyol polyesters may also be used as defoamers, plasticizers, reaction modifiers, and the like. Yet additional uses will be apparent to those skilled in the art in view of the present description.

The following example is intended to further clarify the invention and should not be construed as limiting in any respect. In the examples and throughout, all ratios are molar ratios unless otherwise specified, and percentages are by weight unless otherwise specified.

EXAMPLE

A one-stage reaction is used to produce polyol fatty acid polyester. Basic catalyst ($K_2CO_3$), $C_8$ methyl ester, sucrose and $C_{22}$ fatty acid soap are mixed to form an initial reaction mixture. The molar ratio of methyl ester/sucrose/soap is about 12:1:0.75. The initial reaction mixture is heated at about 135° C. and the pressure is decreased from about 250 mm Hg at the start of heating to about 65 mm Hg at the end of the heating so as to maintain a constant reflux rate of $C_8$ methyl ester.

The reaction is recatalyzed once with $K_2CO_3$ after about one hour (about 0.1 mole catalyst per mole of sucrose is added) and once with $KOCH_3$ after about three hours (about 0.1 mole catalyst per mole of sucrose is added).

About 90% conversion to sucrose octaester is achieved in about five hours' total reaction time. Kinetic results are set forth in Table 1.

TABLE 1

| Kinetic Results | | | |
|---|---|---|---|
| Time (Hrs) | % $SE_8$ | Degree of Esterification | Pressure (mm Hg) |
| 1 | — | 1.99 | 185 |
| 2 | 45.4 | 6.86 | 105 |
| 3 | 74.7 | 7.57 | 85 |
| 4 | 83.0 | 7.69 | 65 |
| 5 | 90.0 | 7.89 | 65 |

$SE_8$ = Sucrose Octaester

The reaction mix becomes slightly more viscous at after about two hours, but less viscous than as experienced in a reaction employing a methyl ester/sucrose/soap molar ratio of about 5:1:0.75. The methanol level measured after about three hours is about 50 ppm.

Having described the preferred embodiments of the present invention, further adaptions of the processes described herein can be accomplished by appropriate modifications by one of ordinary skill in the art without departing from the scope of the present invention. A number of alternatives and modifications have been described herein, and others will be apparent to those skilled in the art. Accordingly, the scope of the present invention should be considered in terms of the following claims, and is understood not to be limited to the details of the processes described in the specification.

All documents cited are, in relevant part, incorporated herein by reference; the citation of any document is not to be construed as an admission that it is prior art with respect to the present invention.

The invention claimed is:

1. A process for the preparation of polyol fatty acid polyester, comprising heating a mixture of polyol, fatty acid ester, emulsifying agent and catalyst under conditions sufficient to cause reaction of the polyol and the fatty acid ester, wherein the fatty acid chains of the fatty acid ester have from about 6 to about 14 total carbon atoms, wherein the emulsifying agent comprises a fatty acid soap having fatty acid chains of from about 16 to about 22 total carbon atoms, and wherein the mixture is heated at a pressure sufficient to maintain a substantially constant reflux rate of the fatty acid ester during the reaction of the polyol and the fatty acid ester.

2. A process according to claim 1, wherein the process further comprises the step of adding additional fatty acid ester after reaction of the polyol and original fatty acid ester has begun.

3. A process according to claim 1, wherein the degree of esterification of the polyol fatty acid polyester is at least about 70%.

4. A process according to claim 1, wherein the fatty acid chains of the fatty acid ester have from about 8 to about 12 total carbon atoms.

5. A process according to claim 1, wherein the fatty acid chains of the fatty acid ester have from about 8 to about 10 total carbon atoms.

6. A process according to claim 4, wherein the fatty acid ester comprises a branched chain fatty acid ester.

7. A process according to claim 6, wherein the fatty acid ester is prepared from an acid having the structure:

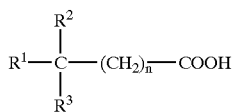

wherein $R^1$ is a hydrocarbon, $R^2$ and $R^3$ are independently selected from hydrogen and a hydrocarbon, n is from 0 to about 11 and the acid has from about 6 to about 14 carbon atoms.

8. A process according to claim 1, wherein the fatty acid ester is obtained from an oil selected from the group consisting of coconut oil, fractionated coconut oil, and mixtures thereof.

9. A process according to claim 8, wherein the pressure is decreased during the heating step.

10. A process according to claim 8, wherein the pressure is in the range of from about 60 to about 190 mm Hg.

11. A process according to claim 1, wherein the polyol comprises sucrose.

12. A process according to claim 1, wherein the pour point of the polyol fatty acid polyester is not greater than about −15° C.

13. A process according to claim 1, wherein the mixture is heated at a temperature in the range of from about 115° to about 150° C.

14. A process according to claim 13, wherein the mixture is heated at a temperature of about 135° C.

15. A process according to claim 1, wherein the catalyst is selected from the group consisting of alkali metals; alloys of at least two alkali metals; alkali metal hydrides; alkali metal lower alkyls; alkali metal alkoxides of lower alcohols; carbonates and bicarbonates of alkali metals; carbonates and bicarbonates of alkaline earth metals; and mixtures thereof.

16. A process for the preparation of polyol fatty acid polyesters, comprising heating a mixture of polyol, fatty acid ester and catalyst wherein the fatty acid chains of the fatty acid ester have from about 6 to about 14 total carbon atoms and at least 50% the polyol's hydroxyl groups are esterified and wherein the mixture is heated at a pressure sufficient to maintain a substantially constant reflux rate of the fatty acid ester during the reaction of the polyol and the fatty acid ester.

17. A process according to claim 16, wherein the polyol comprises sucrose.

18. A process according to claim 17, wherein the fatty acid chains of the fatty acid ester have from about 8 to about 12 total carbon atoms.

19. A process according to claim 18, wherein the fatty acid chains of the fatty acid ester have from about 8 to about 10 total carbon atoms.

20. A process according to claim 18, wherein the fatty acid ester comprises a branched chain fatty acid ester.

21. A process according to claim 16, wherein the fatty acid ester is obtained from an oil selected from the group consisting of coconut oil, fractionated coconut oil, and mixtures thereof.

22. A process according to claim 16, wherein the polyol fatty acid polyester has a pour point of not greater than about −15 °C.

23. A process according to claim 16, wherein the mixture further comprises an emulsifying agent comprising a fatty acid soap having fatty acid chains of from about 16 to about 22 total carbon atoms.

24. A process according to claim 16 wherein no emulsifying agent is added to the mixture.

25. A process for the preparation of higher polyol fatty acid polyesters, comprising heating a mixture of polyol, fatty acid ester and catalyst, at a pressure sufficient to maintain a substantially constant reflux rate of the fatty acid ester, to form a polyol fatty acid polyester wherein the polyol fatty acid polyester has a pour point of not greater than about −15 °C.

26. A process according to claim 25, wherein the polyol comprises sucrose and the fatty acid chains of the fatty acid ester have from about 6 to about 14 total carbon atoms.

27. A process according to claim 25, wherein the fatty acid ester comprises a branched chain fatty acid ester.

28. A process according to claim 25, wherein the mixture further comprises an emulsifying agent comprising a fatty acid soap having fatty acid chains of from about 16 to about 22 total carbon atoms.

* * * * *